US00PP08983P

United States Patent [19]

Rowe

[11] Patent Number: Plant 8,983

[45] Date of Patent: Nov. 22, 1994

[54] BANANA PLANT "FHIA-01"

[75] Inventor: Phillip R. Rowe, La Lima, Honduras

[73] Assignee: Fundación Hondureña de Investigación Agrícola, San Pedro Sula, Honduras

[21] Appl. No.: 188,300

[22] Filed: Jan. 28, 1994

[51] Int. Cl.[5] ..... A01H 5/00
[52] U.S. Cl. ..... Plt./33.1
[58] Field of Search ..... Plt. 33.1, 100

[56] References Cited

PUBLICATIONS

Rowe, P. R., "Breeding Bananas and Plantains for Resistance to *Fusarium* Wilt: The Track Record " *Fusarium Wilt of Banana* (Ploetz, R. C., Ed.) 1990 APS Press, pp. 115–119.

*Primary Examiner*—James R. Feyrer
*Attorney, Agent, or Firm*—Pravel, Hewitt, Kimball & Krieger

[57] ABSTRACT

This new and distinct variety of banana plant has the following unique combination of desirable features:

1. High level of resistance to both the yellow Sigatoka leaf spot disease (*Mycosphaerella musicola*) and the black Sigatoka leaf spot disease (*Mycosphaerella fijiensis*).
2. Practical immunity to both races 1 and 4 of Panama disease (*Fusarium oxysporum* f. sp. cubense).
3. A strong root system which makes it a hardy plant under marginal water and soil conditions.
4. Cold tolerant - plant remains green under cold conditions which cause the reference "Williams" Cavendish variety to turn a yellowish color.
5. Excellent green life of fruit after harvest which renders it suitable for export.
6. Sliced or diced green and ripe fruit does not oxidize to an unsightly brownish color as does the fruit of the Cavendish export clones.
7. Pleasant slightly tart flavor when ripe.
8. Peel of harvested green fruit turns yellow when left to ripen under ambient conditons without ethylene treatment.

3 Drawing Sheets

ORIGIN OF THE VARIETY

This new variety was developed at the Fundación Hondureña de Investigación Agrícola (FHIA) at La Lima, Honduras from a cross made in 1982. It was selected in 1985 from several first generation seedlings from the cross Prata Aña×SH-3142 (both unpatented). Prata Aña is a naturally occurring sub-acid (apple like) flavored triploid clone which is grown commercially on a small scale in Brazil. SH-3142, which was developed by inventor, is a bred diploid which is resistant to Panama disease and the burrowing nematode (*Radopholus similis*). SH-3142 was derived by crossing the SH-1734 bred diploid onto the Pisang Jari Buaya natural diploid which was collected from Papua New Guinea. (The diploids on the FHIA germplasm collection which are in the pedigree of SH-1734 are Lidi, Sinwobogi and a *Musa acuminata* subsp. errans wild fully seeded type which was collected as natural clones in Sumatra, Papua New Guinea and the Philippines, respectively.) FHIA-01 was selected as a tetraploid hybrid which maintained the semi-dwarf plant stature of its Prata Aña parental line, but differs from Prata Aña by having a much larger bunch size and a high level of resistance to both races 1 and 4 of Panama disease and to both the yellow and the black Sigatoka diseases. FHIA-01 is also readily distinguished from Prata Aña by the texture of the pulp of ripe fruit. The pulp of FHIA-01 is noticeably softer while the pulp of Pranta Aňa is considerably more firm when compared to the reference Cavendish clones.

ASEXUAL REPRODUCTION OF THE VARIETY

This new banana plant was asexually reproduced by corms as performed by inventor in the experimental farm of FHIA in La Lima, Honduras and shows that all plant and fruit characteristics run true to the original selected plant and are identical in all respects.

SUMMARY OF THE VARIETY

This new and distinct variety of banana is a vigorous semi-dwarf plant which produces large bunches of fruit. Individual fruits differ in size and shape from those of the Cavendish clones (which presently supply more than 99% of the bananas for export markets) by being slightly straighter, by having a more angular shape, and by being thicker in diameter when fully mature. The ripe fruit is slightly softer and has a more tart flavor than fruit of the Cavendish clones. Green life of harvested FHIA-01 fruit is execellent for export purposes and this new plant is, as are the Cavendish clones, resistant to race 1 of Panama disease. This new plant is also practically immune to race 4 of Panama disease and has a high level of resistance to the yellow and black Sigatoka leaf spot diseases which attack the Cavendish clones. Thus, FHIA-01 could be grown with considerably less fungicide usage than that required to control diseases on the current export bananas. The relative lack of oxidation in sliced or diced fruit of this new banana makes it much more attractive than fruit of the Cavendish clones for preparation of dishes such as fruit salads and desserts. Interest in this new variety is that it is the first known bred banana which has disease resistance and fruit quality characteristics which make it a candidate for being cultivated on a large scale.

DESCRIPTION OF THE PHOTOGRAPHS

The accompanying photographic reproductions show typical specimens of the new banana variety.

Figure 2:
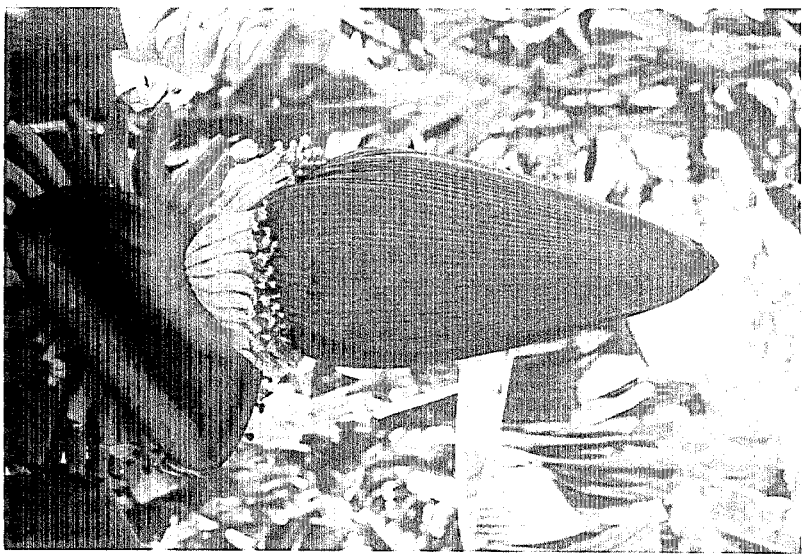
FIG. 2 shows a male bud of a typical FHIA-01 Banana Plant at time of transition from female to male flowers.
Figure 1:
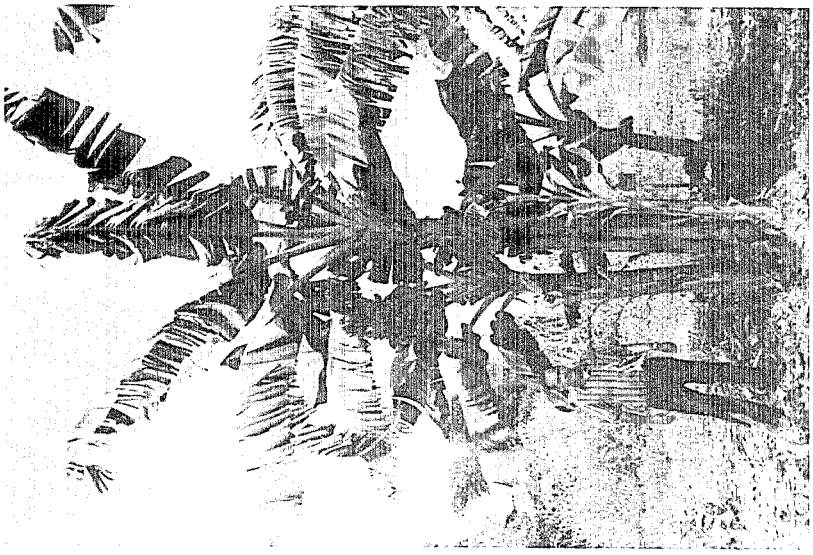
FIG. 1 shows a typical FHIA-01 Banana Plant at time of bunch exposure for the second fruiting cycle.
Figure 4:
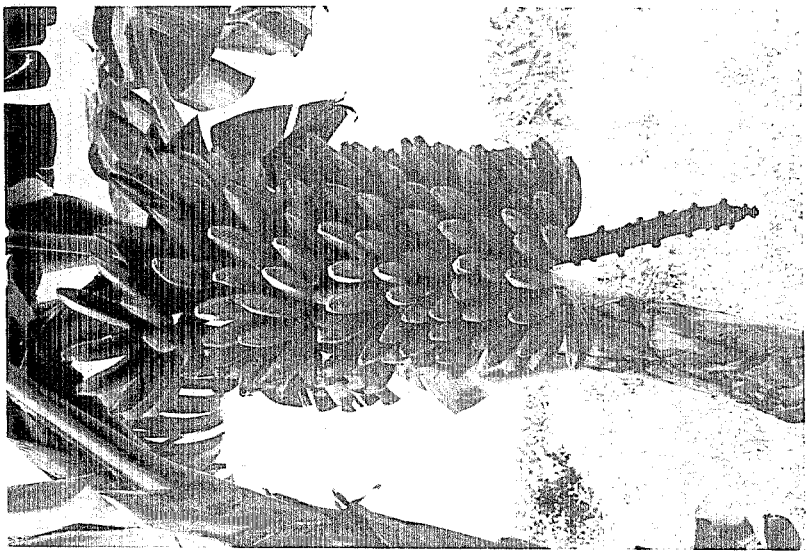
FIG. 4 shows a hanging bunch of the new variety at stage for harvest.
Figure 3:
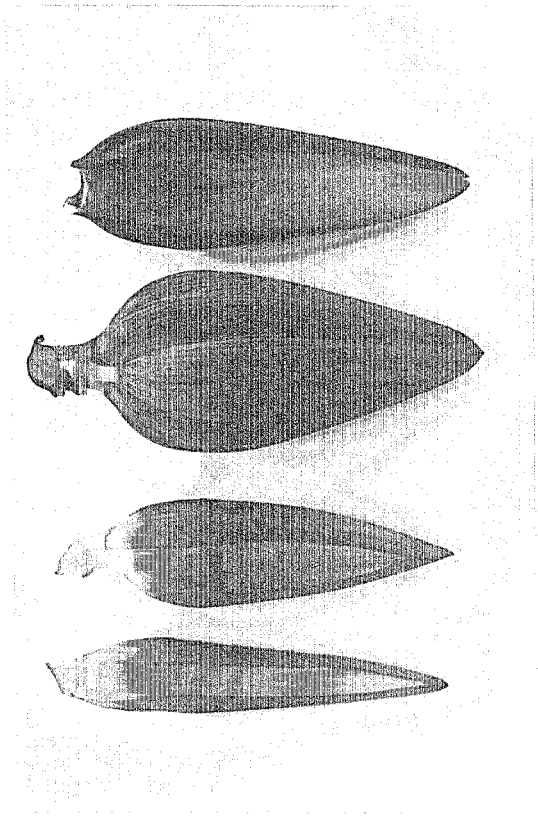
FIG. 3 shows detached newly formed male buds with the outer bract removed before it lifts naturally to depict botanically distinguishing size, shape and color differences in these plant parts of the "Williams" Cavendish reference variety (left) as compared to FHIA-01. Inside surface color of this outer bract for the new variety conforms to Plate 6-K-9.
Figure 5:
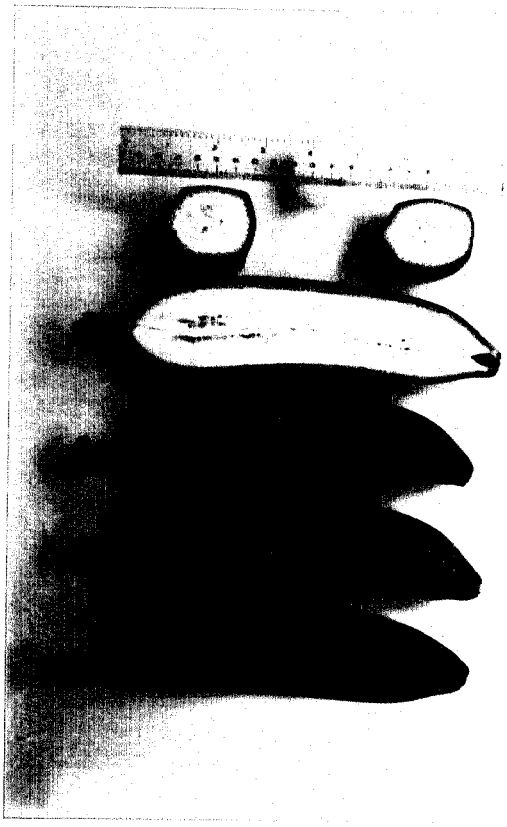
FIG. 5 shows representative whole fingers, a longitudianl section, and cross-sections of fruit at harvest stage of the new variety (marker is 20 cm).

The photographs were taken on fresh material and the colors are as nearly true as is reasonably possible in color representations of this type.

DESCRIPTION OF THE VARIETY

The following is a detailed botanical description of the new and distinct variety of banana plant, its flowers, foliage and fruit as based on observations of specimens grown in the FHIA experimental farm near La aLima, Honduras. These descriptions are in accordance with the internationally standarized "Descriptor List for Bananas" elaborated by the Institut de Recherches sur les Fruits et Agrumes in Montpellier, France. Color terminology for the male bud and bracts, which have very distinctive colors for variety identification, is in accordance with the Maerz and Paul Dictionary of Color. Other colors are given in common terms for bananas.

Vegetative characteristics (General growth/pseudostems/suckers):

*Ploidy.*—Tetraploid (AAAB).
*General appearance.*—Normal.
*Characteristics of dwarfism.*—Yes; height of mother plant as fruit bearing time is 2.7 meters for first fruiting cycle and 3.5 meters for second fruiting cycle.
*Size.*—Large.
*Stature.*—Robust.
*Color of pseudostem.*—Light green.
*Appearance of pse;udostem.*—Shiny.
*Predominant color at the inside base of outer leaf sheath.*—Pink.
*Pigmentation of internal leaf sheaths.*—Pink.
*Color of the sap.*—Milky.
*Wax on leaf sheaths.*—Little.
*Number of suckers* (>30 cm).—From 3 to 5.
*Development of suckers.*—No inhibition.
*Position of growth of suckers.*—Vertical growth.

Vegetative characteristics (Petioles/midribs/leaves):

*Blotches at the base of the petiole.*—Small blotches.
*Color of blotches.*—Dark brown.
*Petiole margins.*—Winged and clasping the pseudostem.
*Type of margin.*—Dry.
*Line of color along edge of petiole margin.*—Yes.
*Color of petiole margin.*—Pink/red.
*Width of petiole margin.*—Wide.
*Length of leaf six.*—Long (220–260 cm).
*Width of leaf six.*—Large (80–90 cm).
*Length of petiole.*—Medium (50–70 cm).
*Color of upper surface of leaf.*—Green.
*Appearance of upper surface of leaf.*—Dull.
*Color of lower surface of leaf.*—Green.
*Appearance of lower surface of leaf.*—Dull.
*Presence of wax on leaves.*—Little.
*Insertion of leaf.*—±Symmetric.
*Base of leaf.*—Both sides rounded.
*Corrugation of leaf.*—Medium corrugation.
*Color of dorsal face of midrib.*—Light green.
*Color of ventral face of midrib.*—Green.
*Color of dorsal face of cigar leaf.*—Green.
*Leaves of young suckers.*—Without blotches.

Inflorescence (General appararance/male bud):

*Length of peduncle.*—Medium.
*Number of empty nodes on peduncle.*—One.
*Size of peduncle.*—Large.
*Color of peduncle.*—Green.
*Hairiness of peduncle.*—Slightly hairy.
*Position of bunch.*—Slightly angled.
*Shape of bunch.*—Cylindrical.
*Appearance of bunch.*—Compact.
*Flowers forming the fruit.*—Female.
*Fingers of the bunch.*—Biseriate.
*Position of rachis.*—At an angle.
*Appearance of rachis.*—Bare.
*Presence of male bud.*—Present.
*Shape of male bud.*—Like a top.
*Size of male bud.*—Large.

Bracts:

*Shape of the base of the bract.*—Large shoulder.
*Shape of apex of bract.*—Intermediate.
*Imbrication of the bract.*—Young bracts slightly overlap.
*Color of the external face of the bract.*—Purple/-brown (Plate 56-E-3).
*Color of the internal face of the naturally lifted bract-.*—Red/crimson (Plate 8-L-7).
*Color of the apex of the bract.*—Not timed with yellow.
*Stripes of color on bract.*—No.
*Bract scars on rachis.*—Very prominent.
*Fading of color at the base of the inside of the bract-.*—Color discontinuing towards the base.
*Shape of the male bract.*—Width/length greater than 0.30.
*Lifting of male bracts.*—Lifting two or more at a time.
*Behavior of bracts.*—Revolute.
*Presence of wax on the bract.*—Little or no wax.
*Presence of grooves on the bract.*—Intermediate.

Male flowers:

*Behavior of male flowers.*—Falling with the bract.
*Basic color of compound tepal.*—Cream.
*Pigmentation of compound tepal.*—Rust-colored spots.
*Color of the lobes of the compound tepal.*—Yellow.
*Development of the lobes of the compound tepal.*—Little development.
*Color of the free tepal.*—Translucent white.
*Shape of the free tepal.*—Oval.
*Appearance of free tepal.*—Folded under apex.
*Apex of the free tepal.*—Medium developed.

*Shape of the apex of free tepal.*—Thread-like.
*Length of anthers.*—Equal to compound tepal.
*Color of filament.*—Cream.
*Color of anther (dorsal face).*—Cream.
*Color of the pollen sacs.*—Brown.
*Pollen.*—Little.
*Basic color of style.*—Cream.
*Purple pigmentation of style.*—Present.
*Length of style.*—Equal to compound tepal.
*Shape of style.*—Curved twice.
*Color of stigma.*—Cream.
*Shape of ovary.*—Straight.
*Basic color of ovary.*—Cream.
*Pigmentation of the ovary.*—Without red/purple.
*Dominant color of male flower.*—Cream.
*Irregular flowers.*—Rare.

Characteristics of the fruit:

*Position of fruit.*—Curved upwards.
*Number of fruits in the middle hand.*—More than 16.
*Length of fruit.*—Medium (20–25 cm).
*Shape of fruit.*—Slightly curved, but with the frequent occurrence of one or more severely curved (with a right angle shape) fingers in the bunch.
*Transverse section of fruit.*—Pronounced ridges.
*Apex of fruit.*—Intermediate.
*Remains of flower parts at apex of fruit.*—Without any floral remains.
*Length of pedicel of fruit.*—Medium.
*Width of pedicel of fruit.*—Large.
*Hairiness of pedicel.*—Not hairy.
*Fusion of pedicels.*—Not fused.
*Color of fruit skin before maturity.*—Pale green.
*Color of skin after maturity.*—Yellow, with absence of or very sparse brown flecks in advanced stage of ripeness.
*Thickness of skin.*—Thick.
*Adherence of the skin.*—Fruit peels easily.
*Presence of cracks in skin.*—No.
*Presence of pulp.*—Yes.
*Color of the pulp before maturity.*—Cream.
*Color of the pulp ater maturity.*—Cream.
*Fruit falling before maturity.*—No.

*Fruit is eaten.*—Green and/or ripe.
*Texture of pulp.*—Soft.
*Taste.*—Sweet-acid.
*Main use.*—Dessert and cooking banana.
*Presence of seeds with source of pollen.*—Few.
*Appearance of seeds.*—Smooth.
*Shape of seeds.*—Flat or rounded.

Agronomic characteristics (Averages taken during 1991–92 for first crop in a plot of 10 plants with no control of diseases):

*Days from planting to first flowering.*—334.
*Number of leaves at flowering.*—16.
*Number of functional leaves (less than* 15% of area necrotic) at flowering.—15.
*Number of leaves at harvest.*—8.
*Number of functional leaves (less than* 15% of area necrotic) at harvest.—4.
*Days from flowering until harvest.*—124.
*Bunch weight.*—28.5 kg.
*Number of hands.*—10.0.
*Finger length.*—21.0 cm.
*Finger diameter.*—3.7 cm.
*Number of fingers per bunch.*—145.0.
*Days from first flowering until second flowering*.—155.

Variance in botanical details:

The banana plant and its fruit described above may vary slightly in detail due to cultural practices, soil types and climate conditions under which the variety may be grown; the present description is that of the variety grown under the ecological conditions prevailing on the FHIA experimental station hear La Lima, Honduras.

I claim:

1. A new and distinct variety of banana plant, substantially as illustrated and described, which is a cold-tolerant and hardy plant with high levels of resistance to the yellow and black Sigatoka leaf spot diseases and practical immunity to races 1 and 4 of Panama disease; the fruit is further characterized by having a pleasant tart flavor, to having an excellent green life which permits it to be exported, and to not oxidizing to an unsightly brownish color when sliced or diced.

* * * * *